United States Patent [19]
McNelis et al.

[11] Patent Number: 5,634,248
[45] Date of Patent: Jun. 3, 1997

[54] METHOD FOR POST FORMING A ROUNDED INSERTION END OF A TAMPON PLEDGET OF AN OPEN-ENDED APPLICATOR

[75] Inventors: Thomas C. McNelis; Jamshid Rejai, both of Dover; Richard A. Weber, Smyrna, all of Del.

[73] Assignee: Playtex Products, Inc., Westport, Conn.

[21] Appl. No.: 502,589

[22] Filed: Jul. 14, 1995

[51] Int. Cl.$^6$ .............................. A61F 13/20; D04H 1/06
[52] U.S. Cl. .................................................. 28/118
[58] Field of Search ........................... 28/118, 119, 120, 28/121, 116, 123; 604/904, 358

[56] References Cited

U.S. PATENT DOCUMENTS

| | | | |
|---|---|---|---|
| 2,355,628 | 8/1944 | Calhoun | 604/904 |
| 2,386,590 | 10/1945 | Calhoun | 604/904 |
| 3,343,225 | 9/1967 | Hochstrasser et al. | 19/144.5 |
| 3,422,496 | 1/1969 | Wolff et al. | 28/118 |
| 3,515,138 | 6/1970 | Hochstrasser et al. | 128/270 |
| 5,330,421 | 7/1994 | Tarr et al. | 604/18 |

*Primary Examiner*—Amy B. Vanatta
*Attorney, Agent, or Firm*—Ohlandt, Greeley, Ruggiero & Perle

[57] ABSTRACT

There is provided a method for forming a round, hemispherical shape at the forward insertion end of a tampon pledget after the pledget has been assembled within a tampon applicator. The pledget is assembled within the applicator so that a portion of its fibers is exposed at an open insertion end of the applicator. After assembly, an insertion end formation tool is applied to the exposed fibers to form a depression in the middle of the insertion end and a full periphery cushion that flares peripherally outward from the depression. The insertion end formation tool has a reverse-donut shaped curvature with a central projection or spike. The central spike reduces the axial force necessary to form the full periphery cushion by radially displacing the fibers in the central location or middle of the insertion end of the pledget. With the insertion end formed in accordance with the method of present invention, the full periphery cushion provides a rounded, forward or insertion end to facilitate an application of the tampon for its intended use.

22 Claims, 2 Drawing Sheets

METHOD FOR POST FORMING A ROUNDED INSERTION END OF A TAMPON PLEDGET OF AN OPEN-ENDED APPLICATOR

BACKGROUND OF THE INVENTION

1. Field of the Invention

The present invention relates generally to tampon pledgets and their relationship to tampon applicators. More particularly, the present invention relates to an improved method for post forming a rounded insertion end of a tampon pledget in an open-ended tampon applicator. The tampon pledget forms a cushion at an open tampon insertion edge of the tampon applicator and yet it is held securely in the applicator in order to be ready for use.

It is known that a rounded insertion end of a tampon assembly, which includes a tampon pledget and a tampon applicator, aids in the insertion of the pledget into a vagina. There are two known methods for forming a rounded insertion end for a tampon assembly. The first is to form rounded, flexible petals at the insertion end of the applicator to cover the blunt insertion end of the pledget. The second is to form a rounded insertion or forward end of the pledget which would be used with an open end of the applicator.

Concerning the latter, a great amount of axial force at the forward end of the pledget is needed to achieve a rounded shape. Also, an opposing force to support the pledget against the axial force is also necessary. In particular, the axial force may exceed the columnar strength of the pledget and, thus, a substantial amount of radial support for maintaining the column integrity of the pledget is required during formation of the rounded forward end of the pledget. Due to the difficulty of providing adequate radial support, existing methods preform the rounded shape at the forward end of the pledget before the pledget is inserted into the applicator. In this manner, the outer cylindrical wall of the pledget can be supported easily and directly since the pledget has not yet been positioned within an applicator. Such a preformed pledget must be carefully inserted, string end first, through the open end of the applicator after forming the rounded forward end in order to preserve the preformed forward end and to provide an adequate fit for holding the pledget. Accordingly, an expensive and complicated process for assembling the tampon assembly has, heretofore, been required.

2. Description of the Prior Art

It has been recognized in the industry that a pledget having a preformed insertion end is desirable. For example, U.S. Pat. No. 3,345,255 to J. Hochstrasser, et al. titled APPARATUS FOR TREATING ELONGATED DEFORMABLE ARTICLES, provides a spiked rotating tool for forming a central depression or recess within the forward end of a tampon pledget. The depression increases the rate of absorption of menstrual fluids at the forward end of the pledget. Similarly, U.S. Pat. No. 3,515,138 to Hochstrasser, et al. titled PROCESS AND APPARATUS FOR TREATING ELONGATED DEFORMABLE ARTICLES is a division of the application that matured into the above-discussed U.S. Pat. No. 3,343,225, and is directed particularly to the above-described pledget.

The above patents provide a method for preforming a central depression in a pledget to increase its absorbency capability, regardless of the material with which it is made. However, they do not provide a method for post forming the depression after the pledget has been inserted in an applicator.

There is a need for a method of producing tampon products by forming the rounded insertion end or forward end of a pledget subsequent to insertion in the applicator. For such a method, the number of steps required to assemble and manufacture the tampon product would be reduced and, accordingly, the time and cost to assemble and manufacture the tampon product would be reduced as well.

In addition, the above patents do not provide a method for shaping the forward end of a pledger over the open end of an applicator in order to form a rounded insertion end for the tampon assembly. In fact, the above patents particularly provide that the insertion end of the pledget be confined and encompassed within applicator. This is presumably to minimize the propensity of the applicator to engage the forward end of the pledget during ejection and, thus, loosen its fibers.

Still further, the above patents do not provide the quicker, simpler and less complex method of the present invention.

SUMMARY OF THE INVENTION

Against the foregoing background, it is a primary object of the present invention to provide a unique method of putting a post-formed rounded shape in the insertion end or forward end of a tampon pledget.

It is another object of the present invention to provide a method for forming a cushion surface that covers the insertion end or open end of a tampon applicator after the pledget has been assembled therein.

It is yet another object of the present invention to provide such a method in which the axial force necessary to form the rounded forward end of the pledget is reduced by using a central projection or spike to radially displace the fibers of the forward end outward over the open end of the applicator. By this method, a wicking channel is formed to draw menstrual fluids toward the central core of the pledget.

It is a further object of the present invention to provide such a method so that the pledget can be assembled from either end of an open-ended or non-petal tip applicator before the rounded forward end is formed.

It is a still further object of the present invention to provide such a method in which the fibers of the forward end of the pledget are equally displaced about the full periphery of the open end of the applicator, thereby forming a rounded, donut-shaped cushion over the open end.

It is still another object of the present invention to provide such a method in which the tampon pledget and applicator are held securely so that the pledget does not slip out of the applicator prior to use.

BRIEF DESCRIPTION OF THE DRAWINGS

The foregoing and still further the objects and advantages of the present invention will be more apparent from the following detailed explanation of the preferred embodiments of the invention in connection with the accompanying drawings.

DETAILED DESCRIPTION OF THE PREFERRED EMBODIMENT

Figure 1:
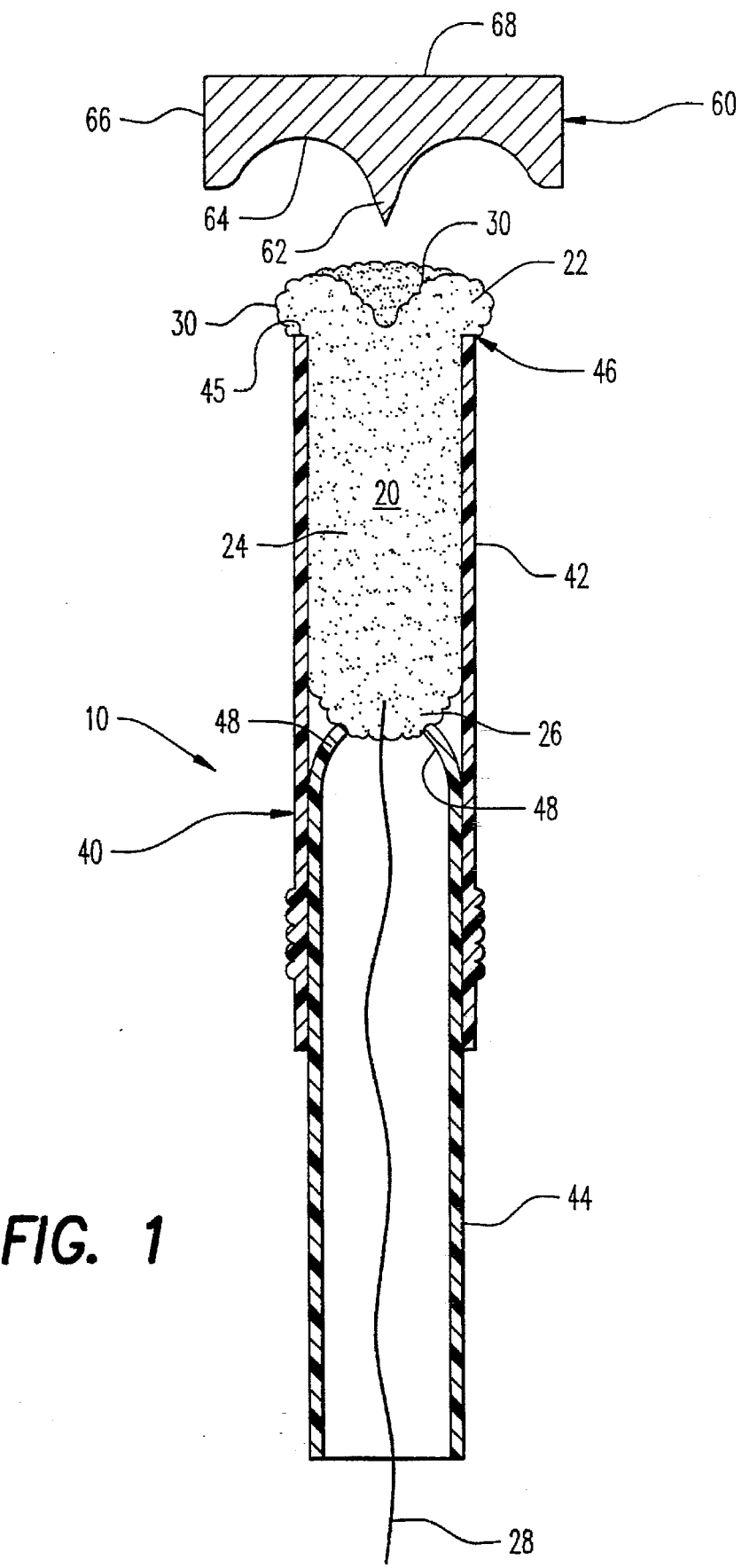
FIG. 1 is a sectional view of the preferred embodiment of the present invention.

Referring to the drawings, and in particular to FIG. 1, there is provided a tampon assembly which is generally represented by reference numeral 10. The tampon assembly 10 includes a tampon pledget 20 and a tampon applicator 40. The tampon applicator 40 has a barrel 42 and a plunger 44. As shown in FIG. 1, the tampon pledget 20 has an insertion end or forward end 22 that has already been formed by the method of the present invention.

As shown in FIG. 1, the forming tool 60 is positioned above the tampon assembly 10. Although the tampon assembly 10 is shown vertically in FIG. 1, the method of the present invention may be performed horizontally (as shown in FIGS. 2A through 2F) or any other way convenient for assembly.

The insertion end 22 of the pledget 20 extends from an open end 46 of the barrel 42 and covers the peripheral edge 45 of the open end 46 of the applicator 40. The insertion end 22 has a donut-like shape. The remainder of the pledget, namely the body 24, is positioned within the inner surface of the barrel 42. Preferably, the body 24 of the pledget slides easily within the inner surface of the barrel 24. The pledget 20 has a rear or back end 26 opposite the insertion end 22, and a draw string 28 that extends from the back end.

For the preferred embodiment, the pledget 20 includes a plurality of fibers 30 that extend into the insertion end 22 as shown in FIG. 1 and the insertion end 22, when positioned in the applicator 40, extends out of the barrel 42. The fibers 30 of the insertion end 22 flare out over the peripheral edge 45 of the barrel 42. The process of forming the insertion end 22 of FIG. 1 is shown in FIGS. 2A through 2F and described below.

It is to be understood that the present invention may be applied for use for a wide variety of tampon applicators. For example, an alternative form of an applicator is set forth in U.S. patent application titled SUPPORTING RIM STRUCTURE OF AN OPEN INSERTION END TAMPON APPLICATOR USED TO POST FORM AN INSERTION END OF A TAMPON PLEDGET, which is owned by the assignee of the present invention. Their application was filed on even date, and is incorporated herein by reference.

The pledget 20 is made of a material having a high liquid absorbency quality. Such materials include rayon, cotton, cotton/rayon blends and paper filler type materials. For the preferred embodiment, the pledget 20 includes a plurality of fibers 30 extending the length of the pledget in order to provide a wicking channel to draw fluids, particularly menstrual fluids, towards the body 24. The pledget 20 is, preferably, made of a cotton/rayon blend.

The plunger 44 of the applicator 40 is slidably mounted within the barrel 42 so that its upper crimped end 48 is adjacent to the back end 26 of the pledget 20. The barrel 42 holds the body 24 of the pledget 20 in order to support the pledget so that its insertion end 22 is exposed from the open end 46. When inserting the pledget 20 into a vagina, the plunger 44 pushes the pledger free from the inner surface of the barrel 42 and through the open end 46.

The materials used in the barrel 42 and plunger 44 of the applicator 40 may be the same material or may vary. The most common materials are the light yet semi-rigid type of materials, including plain or coated paper or cardboard and plastic. The coatings that may be used on the paper or cardboard include, but are not limited to, wax, plastic and cellulose.

The forming tool 60 is situated near the insertion end 22 of the pledget 20 so that it may be moved toward and away from the insertion end. The forming tool, preferably, has a base 68 with a peripheral lip 66 and a concave, reverse donut-shaped groove or circular groove 64. In the middle of the groove 64 is a central projection or spike 62. Measured from the base 68, the spike 62 extends beyond the peripheral lip 66 so that the spike 62 will contact the insertion end 22 prior to the peripheral lip contacting the insertion end. The spiked groove shape of the forming tool 60 reduces the amount of axial force needed to achieve the rounded insertion or forward end 22.

The forming tool 60 may be made of a wide variety of materials that are hard enough to form a rounded shape in the insertion end 22 of a pledget 20. The forming tool 60 may be made of stainless steel or aluminum. In addition, the forming tool 60 may be coated with steel, brass, copper or plastic in order to prevent rust and oxidation. Furthermore, the forming tool 60, and in particular the aluminum, may be anodized to prevent oxidation. The preferred composition of the forming tool is stainless steel.

Optionally, the forming tool may be heated within a temperature range of 150 degrees to 310 degrees Fahrenheit and applied to the insertion end 22 of the pledget 20 for about 3 to about 15 seconds. The temperature and time of heating will depend upon the properties of the fiber materials being formed by the forming tool. Preferably, the forming tool will be heated a temperature of about 210 degrees Fahrenheit for about 7 seconds.

Figure 2A:
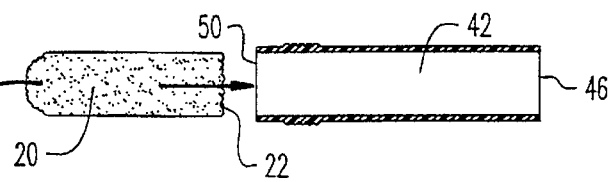
FIGS. 2A through 2F are sectional views of the step-by-step method of the preferred embodiment of FIG. 1.

Referring to generally to FIGS. 2A through 2F, there are shown the six main steps of method of the present invention. As shown in FIG. 2A, the pledget 20 is first inserted into the barrel 42 of the applicator 40. Since the pledget 20 is being inserted before the insertion end 22 has been formed, the pledget may be inserted at the front end 46 or a back end 50 of the barrel 42.

Figure 2B:
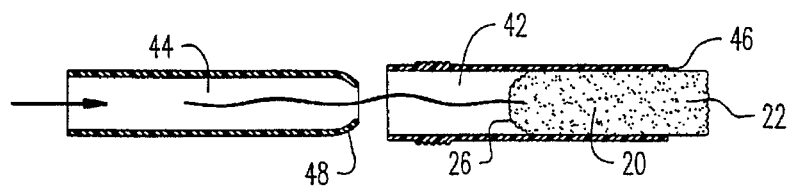

As shown in FIG. 2B, the pledget 20 is then secured at a fixed positioned within the barrel 42 so that the insertion end 22 of the pledget extends beyond the open end 46 of the applicator 40. The plunger 44 is inserted into the barrel 42 so that the crimped end 48 of the plunger is positioned adjacent to the back end 26 of the pledget 20.

Figure 2C:
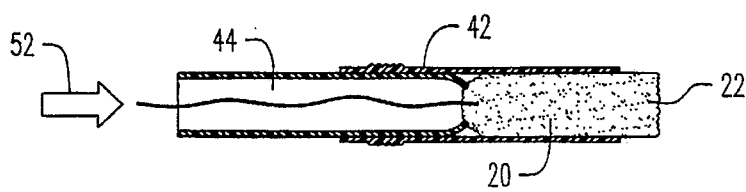

Referring to FIG. 2C, the plunger 44 is then supported at a particular position within the barrel 42 so that the pledget 20 remains at its secured, fixed position. This axial support 52 by the plunger 44 is sustained against the back end 26 of the pledget 20 throughout the formation of the rounded insertion end 22.

Figure 2D:
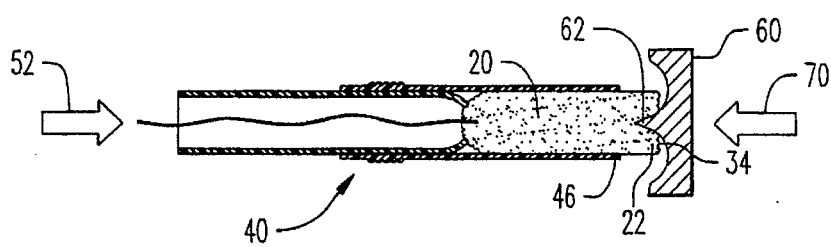

Thereafter, as shown in FIG. 2D, the forming tool 60 is applied to the insertion end 22 of the pledget 20. The central projection or spike 62 of the forming tool 60 is moved towards the insertion end 22 of the pledget 20 by an axial force 70. During this process, the inner fibers of the insertion end 22 are spread peripherally outward so that an outer portion of the insertion end is positioned over and adjacent the edge 45 of the open end 46 of the open-ended applicator 40. In this manner, a substantially radial force is applied to the central location or portion 34 of the insertion end 22 and the fibers 30 (shown in FIG. 1) of the pledget 20 are forced radially outward from the central location.

Figure 2E:
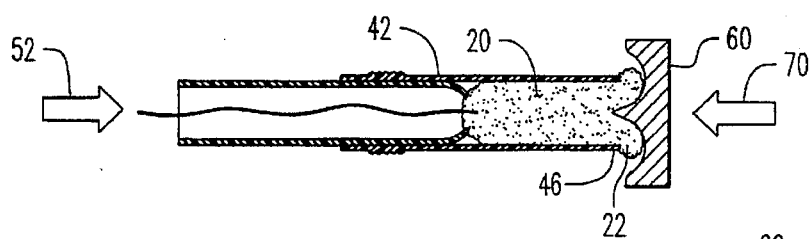

As shown in FIG. 2E, the forming tool 60 is then applied to the insertion end 22 so that a portion of the fibers 30 (shown in FIG. 1) is urged over the edge 45 of the open end 46 of the barrel 42 so as to form the rounded insertion end. Thus, the insertion end 22 of the pledget 20 is molded over the open end 46 of the barrel 42. In this manner, the axial force 70 that applies the forming tool 60 against the insertion end 22 aids to the formation of the rounded insertion end.

Figure 2F:
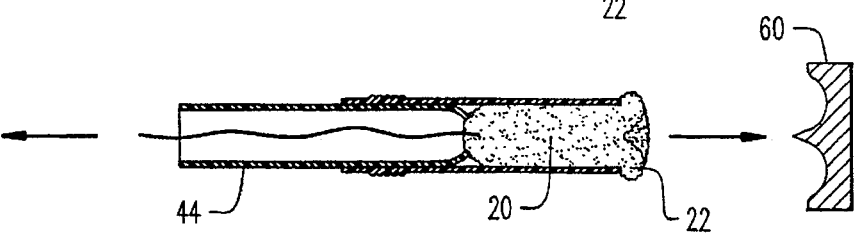

Lastly, as shown in FIG. 2F, the plunger 44 is no longer supported against the pledget 20 and the forming tool 60 is moved away from the insertion end 22 of the pledget.

Figure 3:
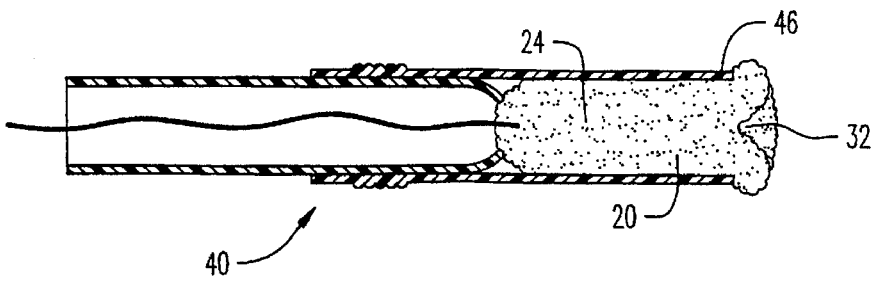
FIG. 3 is a sectional view of the final configuration of the preferred embodiment produced by the steps of FIGS. 2A through F.

FIG. 3 illustrates a final configuration of the preferred embodiment of the present invention, achieved by the steps shown in FIGS. 2A through 2F. Advantageously, the indentation or depression 32 resulting from the spike 62 of the forming tool 60 provides a wicking channel to draw menstrual fluid towards the body 24 of the pledget 20. Further, the spiked groove shape of the forming tool 60 helps to insure that the resulting dome or rounded shape is equally formed around the full circumference of the edge 45 of the open end 46 of the applicator 40, so as to provide a fully periphery cushion for ease of insertion.

The present invention having been thus described with particular reference to the preferred forms thereof, it will be obvious that various changes and modifications may be made therein without departing from the spirit and scope of the invention as defined in the appended claims.

Wherefore, we claim:

1. A method for post forming an insertion end of a tampon pledget after assembly in a tampon applicator having an open front end, the method comprising the steps of:

inserting the tampon pledget into the tampon applicator;

securing the tampon pledget at a fixed position in the tampon applicator; and applying a forming tool having a central projection to the insertion end of the tampon pledget, wherein said central projection spreads the insertion end radially outward and over the front end of the tampon applicator.

2. The method of claim 1, further comprising molding the radially outward insertion end over the front end so that the insertion end has a rounded form.

3. The method of claim 1, wherein the tampon pledget is inserted into the tampon applicator through the front end of the tampon applicator during said inserting step.

4. The method of claim 1, wherein said inserting step includes positioning the tampon pledget in the tampon applicator so that the insertion end of the tampon pledget extends beyond the front end of the tampon applicator.

5. The method of claim 1, wherein said securing step includes supporting the tampon pledget at a back end opposite the insertion end of the tampon pledget.

6. The method of claim 5, wherein said supporting step includes inserting a plunger into the tampon applicator so that one end of the plunger is adjacent to the back end of the tampon pledget.

7. The method of claim 6, wherein said supporting step includes retaining the plunger at a particular position within the tampon applicator so that the tampon pledget remains at the fixed position in the tampon applicator.

8. The method of claim 1, wherein the forming tool has a central spike surrounded by a circular groove, and said applying step includes moving the forming tool in an axial direction towards the insertion end of the tampon pledget.

9. The method of claim 2, further comprising a step of moving the forming tool away from the insertion end of the tampon pledget after the molding step.

10. The method of claim 1, further comprising a step of heating the forming tool before applying the forming tool to the insertion end of the tampon pledget.

11. The method of claim 2, wherein said molding step includes forming the insertion end of the tampon pledget so that the insertion end has a full periphery cushion that flares peripherally outward from a central depression of the insertion end.

12. A method for post forming a round insertion end of a tampon pledget after assembly in an open front end of a tampon applicator, the method comprising the steps of:

inserting the tampon pledget into the tampon applicator;

securing the tampon pledget at a fixed position in the tampon applicator;

applying a substantially radial force at a central location of an insertion end of the tampon pledget, wherein the insertion end is spread radially outward over the open front end of the tampon applicator; and applying an axial force to the insertion end of the tampon pledget over the open front end of the tampon applicator so that the insertion end has a rounded form.

13. The method of claim 12, wherein the pledget is inserted into said applicator through the open front end during said inserting step.

14. The method of claim 12, wherein said inserting step includes positioning the tampon pledget in the tampon applicator so that the insertion end of the tampon pledget extends beyond the open front end of the tampon applicator.

15. The method of claim 12, wherein said securing step includes supporting the tampon pledget at a back end opposite the insertion end of the tampon pledget.

16. The method of claim 15, wherein said supporting step includes inserting a plunger into the tampon applicator so that one end of the plunger is adjacent to the back end of the tampon pledget.

17. The method of claim 16, wherein said supporting step includes retaining the plunger at a particular position within the tampon applicator so that the tampon pledget remains at the fixed position in the tampon applicator.

18. The method of claim 12, wherein the step of applying the axial force occurs during the application of the radial force at the central location of the insertion end of the tampon pledget.

19. The method of claim 12, wherein said step of applying said substantially radial force includes moving a forming tool having a central spike surrounded by a circular groove in an axial direction towards the insertion end of the tampon pledget.

20. The method of claim 12, wherein said step of applying an axial force to the insertion end of the tampon pledget includes forming the insertion end so that the insertion end has a full periphery cushion that flares peripherally outward from a central depression of the insertion end.

21. A method for post forming an insertion end of a tampon pledget after assembly in a tampon applicator having an open front end, the method comprising the steps of:

inserting the tampon pledget into the tampon applicator;

securing the tampon pledget at a fixed position in the tampon applicator; and applying a forming tool to the insertion end of the tampon pledget, wherein said forming tool spreads the insertion end radially outward.

22. The method of claim 21, wherein said forming tool spreads the insertion end of the tampon pledget over the front end of the tampon applicator.

* * * * *